(12) United States Patent
Asai et al.

(10) Patent No.: US 8,579,818 B2
(45) Date of Patent: Nov. 12, 2013

(54) ULTRASONIC DIAGNOSTIC APPARATUS

(75) Inventors: Akimasa Asai, Tokyo (JP); Kazuhiko Hayakawa, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 753 days.

(21) Appl. No.: 12/695,862

(22) Filed: Jan. 28, 2010

(65) Prior Publication Data

US 2010/0191122 A1    Jul. 29, 2010

(30) Foreign Application Priority Data

Jan. 29, 2009   (JP) .................................. 2009-018107

(51) Int. Cl.
   *A61B 8/00*   (2006.01)
(52) U.S. Cl.
   USPC ......................................................... 600/443
(58) Field of Classification Search
   USPC .................................. 600/437–461
   See application file for complete search history.

(56) References Cited

U.S. PATENT DOCUMENTS

| | | | | |
|---|---|---|---|---|
| 4,671,522 A * | 6/1987 | Fragione, Jr. | ............... | 280/47.25 |
| D340,770 S * | 10/1993 | Ohnuma et al. | ............. | D24/186 |
| 5,316,328 A * | 5/1994 | Bussinger | .................. | 280/304.1 |
| 5,351,774 A * | 10/1994 | Okamoto | ..................... | 180/65.1 |
| 6,311,941 B1 * | 11/2001 | Feldmeyer | ................. | 248/188.8 |
| 6,669,639 B1 | 12/2003 | Miller et al. | | |
| 2006/0261654 A1 * | 11/2006 | Stallman | ....................... | 297/310 |
| 2008/0132786 A1 | 6/2008 | Asai et al. | | |

FOREIGN PATENT DOCUMENTS

| | | | |
|---|---|---|---|
| JP | 2004-344636 | 12/2004 | |
| JP | 2008-142331 | 6/2008 | |
| WO | 2005/074806 | 8/2005 | |
| WO | WO 2005074806 A1 * | 8/2005 | ............... A61B 8/00 |

* cited by examiner

*Primary Examiner* — Elmer Chao
(74) *Attorney, Agent, or Firm* — Armstrong Teasdale LLP

(57) ABSTRACT

An ultrasonic diagnostic apparatus includes an ultrasonic diagnostic apparatus body, a support member provided in the ultrasonic diagnostic apparatus body to support the ultrasonic diagnostic apparatus body on an installation surface, a movable body provided in the ultrasonic diagnostic apparatus body in a movable state by a moving member while protruding from the ultrasonic diagnostic apparatus body in a direction away from the ultrasonic diagnostic apparatus body, and a tipping-preventing support member provided in the ultrasonic diagnostic apparatus body and having a support portion able to support the ultrasonic diagnostic apparatus body on the installation surface on the protruding side of the movable body with respect to the support member.

11 Claims, 14 Drawing Sheets

ULTRASONIC DIAGNOSTIC APPARATUS

CROSS REFERENCE TO RELATED APPLICATIONS

This application claims the benefit of Japanese Patent Application No. 2009-018107 filed Jan. 29, 2009, which is hereby incorporated by reference in its entirety.

BACKGROUND OF THE INVENTION

The embodiments described herein relate to an ultrasonic diagnostic apparatus.

An ultrasonic diagnostic apparatus for radiating an ultrasonic wave to a subject and imaging the subject is provided with a monitor for displaying an ultrasonic image. As the monitor, an LCD (Liquid Crystal Display) has recently come to be used. By using an LCD as the monitor, the monitor is reduced in both thickness and weight and consequently the monitor can be attached to the body of the ultrasonic diagnostic apparatus through a plurality of horizontally pivoting arms (see, for example, Japanese Patent Laid-Open Publication No. 2008-142331). The plural arms are adapted to pivot in the horizontal direction, whereby the monitor can move within a horizontal plane. In case of seeing an ultrasonic image displayed on the monitor while making transmission and reception of an ultrasonic wave with an ultrasonic probe abutted on a subject, the monitor can be moved to a position easy to see the image by protruding the monitor from the ultrasonic diagnostic apparatus body.

Recently there has been a demand for enlarging the moving range so that the monitor can be moved to a position easier to see an ultrasonic image. On the other hand, the ultrasonic diagnostic apparatus body tends to become reduced in weight. Therefore, when the movement range of the monitor is enlarged and when the monitor is moved so as to protrude from the ultrasonic diagnostic apparatus body, the center of gravity in the ultrasonic diagnostic apparatus shifts to the protruding side of the monitor with respect to wheels which support the ultrasonic diagnostic apparatus, resulting in that the fear of tipping increases.

BRIEF DESCRIPTION OF THE INVENTION

In a first aspect of the invention there is provided an ultrasonic diagnostic apparatus including an ultrasonic diagnostic apparatus body, a support member provided in the diagnostic apparatus body to support the ultrasonic diagnostic apparatus body on an installation surface, a movable body provided in the ultrasonic diagnostic apparatus body in a movable state by a moving member while protruding from the ultrasonic diagnostic apparatus body in a direction away from the ultrasonic diagnostic apparatus body, and a tipping-preventing support member provided in the ultrasonic diagnostic apparatus body and having a support portion able to support the ultrasonic diagnostic apparatus body on the installation surface on the protruding side of the movable body with respect to the support member.

In a second aspect of the invention there is provided, in combination with the invention of the first aspect, an ultrasonic diagnostic apparatus wherein the support position on the installation surface by the support portion of the tipping-preventing support member is on the protruding side of the movable body with respect to a centroid projected position resulting from projecting the center of gravity of the ultrasonic diagnostic apparatus onto the installation surface downwards in the vertical direction.

In a third aspect of the invention there is provided, in combination with the invention of the first or the second aspect, an ultrasonic diagnostic apparatus wherein the support portion of the tipping-preventing support member is movable between a support position able to support the ultrasonic diagnostic apparatus body and a stand-by position closer to the ultrasonic diagnostic apparatus body than the support position.

In a fourth aspect of the invention there is provided, in combination with the invention of any of the first to third aspects, an ultrasonic diagnostic apparatus further including a movement inhibition device for inhibiting the movement of the movable body by the moving member.

In a fifth aspect of the invention there is provided, in combination with the invention of the fourth aspect, an ultrasonic diagnostic apparatus wherein the movement inhibition device cancels the inhibition when the ultrasonic diagnostic apparatus body is in a state capable of being supported by the support portion of the tipping-preventing support member.

In a sixth aspect of the invention there is provided, in combination with the invention of the fifth aspect, an ultrasonic diagnostic apparatus wherein the support portion of the tipping-preventing support member can ascend and descend with respect to the installation surface and, when it is in a descended position thereof, can support the ultrasonic diagnostic apparatus body on the installation surface, and the movement inhibition device cancels the inhibition when the support portion is in the descended position.

In a seventh aspect of the invention there is provided, in combination with the invention of the sixth aspect, an ultrasonic diagnostic apparatus wherein the descended position of the support portion is a position where the support portion is in contact with the installation surface or a position where the support portion has reached a vicinity of the installation surface.

In an eighth aspect of the invention there is provided, in combination with the invention of any of the fourth to seventh aspects, an ultrasonic diagnostic apparatus wherein the support portion of the tipping-preventing support member is movable between a support position able to support the ultrasonic diagnostic apparatus body and a stand-by position closer to the ultrasonic diagnostic apparatus body than the support position, and the movement inhibition device cancels the inhibition when the support portion is in the support position.

In a ninth aspect of the invention there is provided, in combination with the invention of any of the first to eighth aspects, an ultrasonic diagnostic apparatus wherein in interlock with the movement of the movable body the support portion of the tipping-preventing support member moves between a support position able to support the ultrasonic diagnostic apparatus body and a stand-by position closer to the ultrasonic diagnostic apparatus body than the support position.

In a tenth aspect of the invention there is provided, in combination with the invention of any of the third to ninth aspects, an ultrasonic diagnostic apparatus wherein the support portion of the tipping-preventing support member is movable between the support position and the stand-by position by describing a circular path in the horizontal direction.

In an eleventh aspect of the invention there is provided, in combination with the invention of any of the third to ninth aspects, an ultrasonic diagnostic apparatus wherein the support portion of the tipping-preventing support member is movable between the support position and the stand-by position by describing a rectilinear path in the horizontal direction.

In a twelfth aspect of the invention there is provided, in combination with the invention of any of the third to ninth aspects, an ultrasonic diagnostic apparatus wherein the support portion of the tipping-preventing support member can support between the support position and the stand-by position by moving in an inclined direction relative to the installation surface.

In a thirteenth aspect of the invention there is provided, in combination with the invention of any of the first to twelfth aspects, an ultrasonic diagnostic apparatus wherein the movable body is a flat panel display.

In a fourteenth aspect of the invention there is provided, in combination with the invention of any of the first to thirteenth aspects, an ultrasonic diagnostic apparatus wherein the moving member is an arm adapted to pivot in the horizontal direction.

In fifteenth aspect of the invention there is provided, in combination with any of the first to fourteenth aspects, an ultrasonic diagnostic apparatus wherein the support member is a wheel provided in a lower portion of the ultrasonic diagnostic apparatus body.

According to some embodiments, since the ultrasonic diagnostic apparatus body can be supported by the tipping-preventing support member on the movable body protruding side with respect to the support member, it is possible to prevent tipping of the ultrasonic diagnostic apparatus.

Since the support position on the installation surface by the support portion of the tipping-preventing support member is on the movable body protruding side with respect to the centroid projected position resulting from projecting the center of gravity of the ultrasonic diagnostic apparatus onto the installation surface downwards in the vertical direction, the ultrasonic diagnostic apparatus can be supported by the tipping-preventing support member.

Since the support portion of the tipping-preventing support member is movable between the support position able to support the ultrasonic diagnostic apparatus body and the stand-by position closer to the ultrasonic diagnostic apparatus body than the support position, when the support portion lies in the position where the ultrasonic diagnostic apparatus body can be supported by only the support member, it is possible to prevent the support portion of the tipping-preventing support member from becoming an obstacle, by locating the support portion in the stand-by position.

By making the movement inhibition device cancel the inhibition of the movement by the moving body when the ultrasonic diagnostic apparatus body can be supported by the tipping-preventing support member, the movement of the movable body by the moving member is inhibited by the movement inhibition device when the tipping-preventing support member is in a state unable to support the ultrasonic diagnostic apparatus body. Thus, the tipping of the ultrasonic diagnostic apparatus can be surely prevented.

Further, even when the movable body is moved, the tipping of the ultrasonic diagnostic apparatus can be surely prevented since the support portion of the tipping-preventing support member moves between the support position and the stand-by position in interlock with the movement of the movable body.

DETAILED DESCRIPTION OF THE INVENTION

Figure 1:
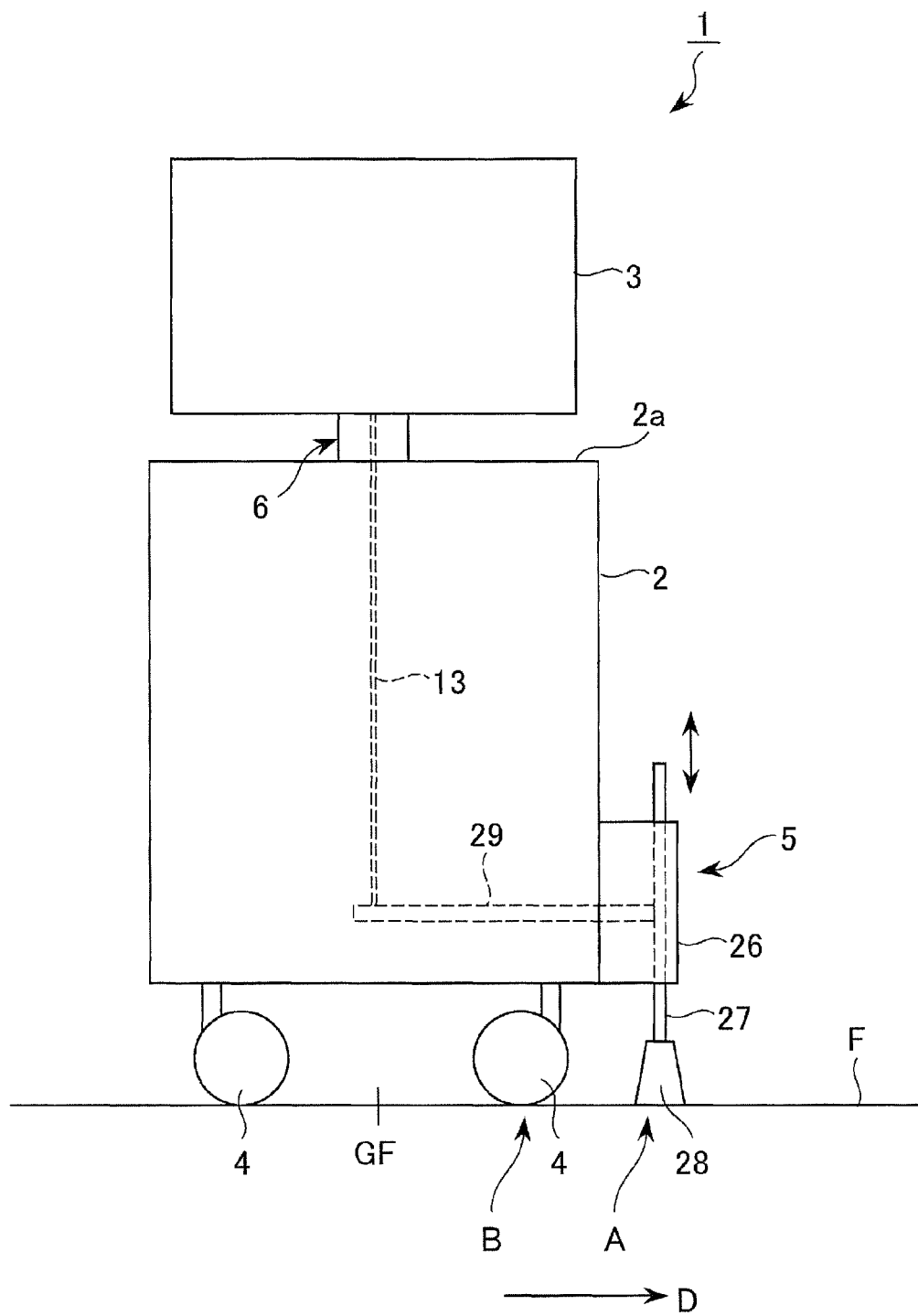
FIG. 1 is a front view showing an ultrasonic diagnostic apparatus according to a first embodiment of the invention.

Embodiments of the invention will be described below in detail with reference to the drawings.

First Embodiment

A first embodiment of the invention will first be described with reference to FIGS. 1 to 8. An ultrasonic diagnostic apparatus 1 includes an ultrasonic diagnostic apparatus body 2 and a display unit 3 provided in the ultrasonic diagnostic apparatus body 2. The ultrasonic diagnostic apparatus body 2 is supported on an installation surface F by wheels 4 provided at a lower portion of the ultrasonic diagnostic apparatus body 2. A tipping-preventing support member 5 is provided sideways of the ultrasonic diagnostic apparatus body 2.

An ultrasonic probe (not shown) for transmission and reception of an ultrasonic wave to and from a subject is connected to the ultrasonic diagnostic apparatus body 2. A processor (not shown) is provided within the ultrasonic diagnostic apparatus body 2. With the processor, an ultrasonic image is produced in accordance with an echo signal obtained by transmission and reception of an ultrasonic wave performed with the ultrasonic probe.

Figure 2:
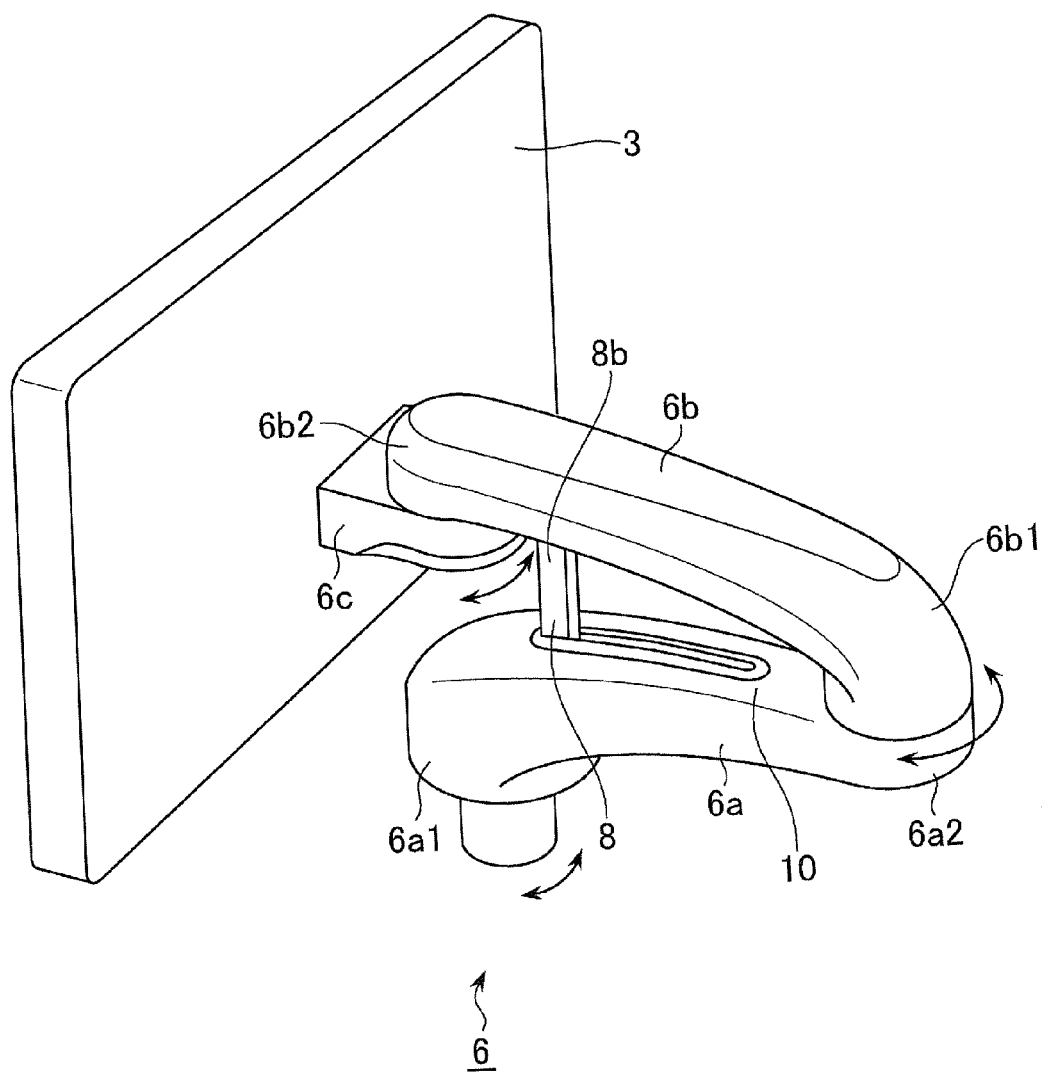
FIG. 2 is a perspective view showing an arm and a display unit used in the ultrasonic diagnostic apparatus of FIG. 1.
Figure 3:
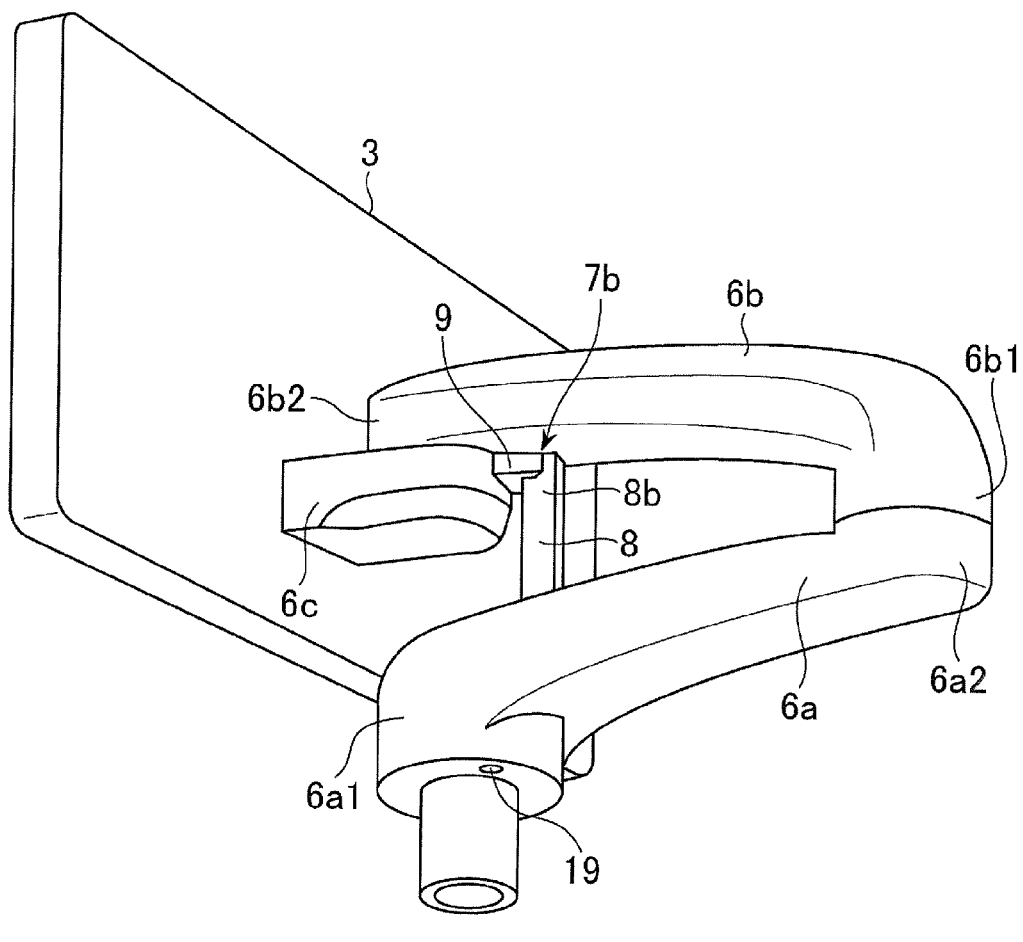
FIG. 3 is a perspective view of the arm and display unit shown in FIG. 2 and seen from another angle.
Figure 7:
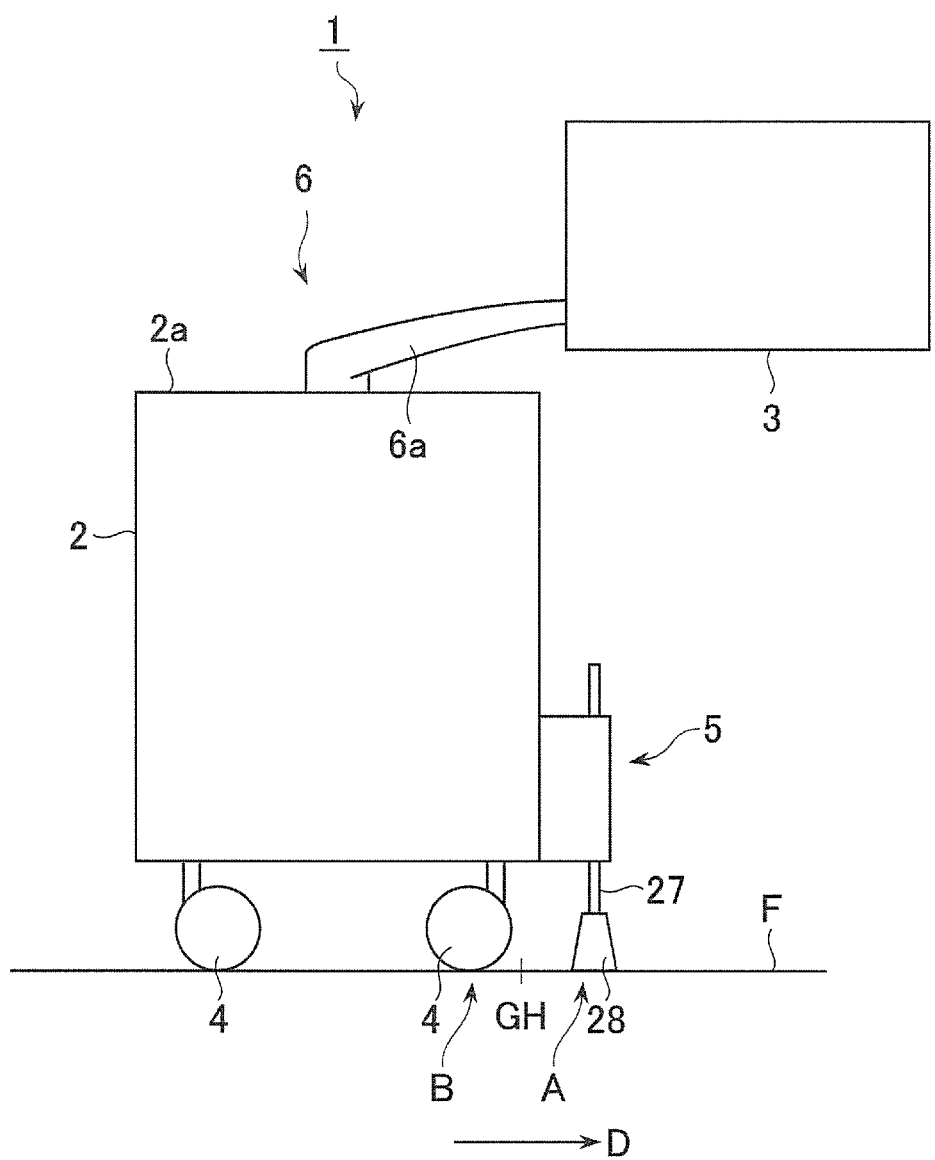
FIG. 7 is a front view of the ultrasonic diagnostic apparatus of the first embodiment, showing a protruded state of the display unit from the ultrasonic diagnostic apparatus body.

The ultrasonic image thus produced is displayed on the display unit 3. The display unit 3 is a flat panel display and is provided in the ultrasonic diagnostic apparatus body 2 through an arm 6. The display unit 3 is provided in the ultrasonic diagnostic apparatus body 2 in a state in which it can be moved in a direction away from the ultrasonic diagnostic apparatus body 2 by the arm 6. More specifically, as shown in FIGS. 2 and 3, the arm 6 is made up of a first arm 6a, a second arm 6b and a third arm 6c. In the first arm 6a, one end portion 6*a*1 is provided on an upper surface 2*a* of the ultrasonic diagnostic apparatus body 2 in a horizontally pivotal state. An opposite end portion 6*a*2 of the first arm 6*a* and one end portion 6*b*1 of the second arm 6*b* are connected together pivotally in the horizontal direction. An opposite end portion 6*b*2 of the second arm 6*b* and the third arm 6*c* are also connected together pivotally in the horizontal direction. Therefore, by pivoting the arms 6*a*-6*c* horizontally, as shown in FIG. 7, the display unit 3 can be moved from its state shown in FIG. 1 in a direction (protruding direction) away from the ultrasonic diagnostic apparatus body 2 so as to protrude from the body 2 so that it becomes easier for an operator to see the display unit 3 at the time of transmission or reception of an ultrasonic wave by the ultrasonic probe. The arm 6 is an example of the moving member defined in the invention and the display unit 3 is an example of the movable body defined in the invention.

Figure 4A:
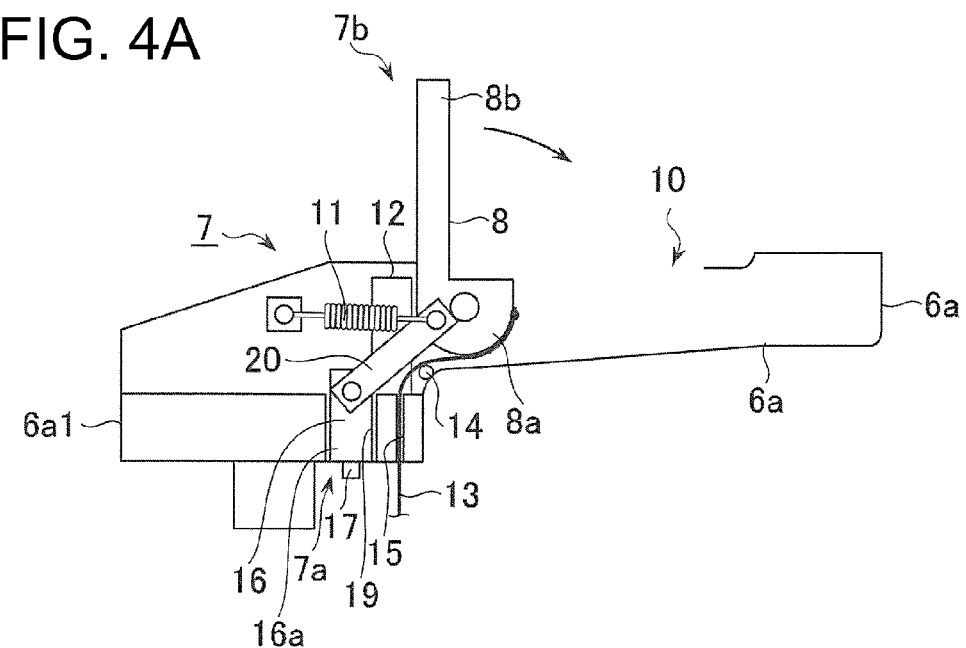
FIGS. 4A and 4B are schematic diagrams showing the interior of a first arm illustrated in FIGS. 2 and 3.
Figure 4B:
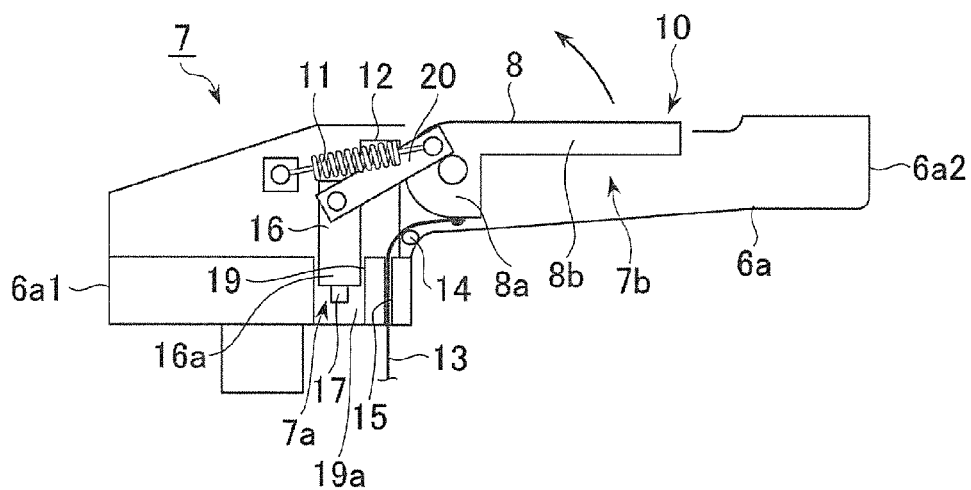

The arms 6*a*-6*c* are inhibited from pivoting in the horizontal direction by a locking mechanism 7 (see FIGS. 4A and 4B). The arms 6*a*-6*c* are inhibited from pivoting horizontally when they face in a direction perpendicular to the front face of the ultrasonic diagnostic apparatus 1 (home position of the arm 6), that is, when the first and second arms 6*a*, 6*b* overlap each other and the second and third arms 6*b*, 6*c* are aligned with each other. The details of this point will be described later. The locking mechanism 7 is an example of the movement inhibition device defined in the invention.

A concrete configuration of the locking mechanism 7 will now be described. The locking mechanism 7 is made up of a first locking mechanism 7*a* (see FIGS. 4A and 4B) for inhibiting a pivotal motion of the first arm 6*a* with respect to the ultrasonic diagnostic apparatus body 2, a second locking mechanism 7*b* (see FIGS. 3 and 4) for inhibiting a mutual pivoting motion of the first and second arms 6*a*, 6*b*, and a third locking mechanism 7*c* (see FIG. 6) for inhibiting a mutual pivotal motion of the second and third arms 6*b*, 6*c*.

The locking mechanisms 7*a*-7*c* will now be described concretely. First, a description will be given about the second locking mechanism 7*b*. The second locking mechanism 7*b* includes a pivoting member 8 provided in the first arm 6*a* and a to-be-fitted member 9 provided on the underside of the second arm 6*b* and in which the pivoting member 8 is fitted. As shown in FIGS. 4A and 4B, the pivoting member 8 is made up of a generally semi-disc-like base portion 8*a* and a rod-like hook portion 8*b*. The base portion 8*a* is provided pivotally within a storage hole 10 formed in the first arm 6*a*. The pivoting member 8 is adapted to pivot within a plane along the longitudinal direction of the first arm 6*a*.

The hook portion 8*b*, when assuming its horizontal position shown in FIG. 4B, is stored within the storage hole 10 formed in the longitudinal direction of the first arm 6*a*. When the hook portion 8*b* lies at its vertical position shown in FIG. 4A after leaving the storage hole 10 and when the first and second arms 6*a*, 6*b* are overlapping each other, the hook portion 8*b* is fitted in a cutout portion 9*a* (see FIG. 6) of the to-be-fitted member 9, whereby a mutual pivoting motion of the first and second arms 6*a*, 6*b* is inhibited.

A further description will now be given about the pivoting member 8. A spring member 11 is anchored at one end thereof to the base portion 8*a* and at an opposite end thereof to an inner wall surface of the first arm 6*a*. With the spring member 11, the pivoting member 8 is urged toward the one end portion 6*a*1 of the first arm 6*a*. As shown in FIG. 4A, the pivoting member 8, when assuming its vertical position, is pushed against a stationary member 12 with a pulling force of the spring member 11, the stationary member 12 being provided on the one end portion 6*a*1 side with respect to the pivoting member 8. On the other hand, a wire 13 is connected at one end thereof to the base portion 8*a* and at an opposite end thereof to a connecting rod 29 which will be described later. When the wire 13 is pulled downward as will be described later, the pivoting member 8 pivots toward the opposite end portion 6*a*2 against the pulling force of the spring member 11 and the hook portion 8*b* is stored within the storage hole 10, as shown in FIG. 4B. A guide roller 14 for guiding the wire 13 is provided in the interior of the first arm 6*a* and the wire 13 is guided with the guide roller 14 into a wire insertion hole 15 formed in the one end portion 6*a*1. The wire 13 passes through the wire insertion hole 15, then through the interior of the ultrasonic diagnostic apparatus body 2 and reaches the connecting rod 29.

Next, a description will be given about the first locking mechanism 7*a*. The first locking mechanism 7*a* includes a plunger 16 disposed in the interior of the first arm 6*a*, a first rod 17 provided in the plunger 16, and a first rod hole 18 (see FIG. 5) formed in the upper surface 2*a* of the ultrasonic diagnostic apparatus body 2. More particularly, in the one end portion 6*a*1 of the first arm 6*a* is formed a plunger hole 19 which opens to the surface opposed to the upper surface 2*a* of the ultrasonic diagnostic apparatus body 2. The plunger 16 is disposed within the plunger hole 19. The plunger 16, at an end portion thereof positioned on the side opposite to an opening 19*a* of the plunger hole 19, is connected to the pivoting member 8 through a link 20. According to this configuration, as the pivoting member 8 pivots, the plunger 16 moves vertically through the interior of the plunger hole 19. As shown in FIG. 4A, when the pivoting member 8 lies at its vertical position, a lower end portion 16*a* in the figure of the plunger 16 descends to the opening 19*a* of the plunger hole 19. On the other hand, as shown in FIG. 4B, when the pivoting member 8 lies at its horizontal position, the plunger 16 ascends up to the position at which the first rod 17 projecting from the lower end portion of the plunger gets into the plunger hole 19.

The first rod 17 is incorporated within the plunger 16. With the biasing force of a spring (not shown) disposed within the plunger 16, a lower end portion of the first rod 17 projects from the lower end portion of the plunger 16. When the pivoting member 8 lies at its horizontal position, the first rod 17 projects within the plunger hole 19. As will be described later, the first rod 17 coincides with the position of the first rod hole 18. When the pivoting member 8 pivots from the horizontal position to the vertical position in this state, the first rod 17 projects from the lower end portion of the plunger 16 in the interior of the first rod hole 18. With the first rod 17 projected into the first rod hole 18, the pivoting motion of the first arm 6*a* with respect to the ultrasonic diagnostic apparatus body 2 is inhibited.

On the other hand, in a pivoted state of the pivoting member 8 from its horizontal position to its vertical position and with the first rod 17 not positioned over the first rod hole 18, the first rod 17 is pushed against the upper surface 2*a* of the ultrasonic diagnostic apparatus body 2 and retreats into the plunger 16 against the biasing force of the aforesaid spring. In this state, the first arm 6*a* is pivotal with respect to the ultrasonic diagnostic apparatus body 2.

When the pivoting member 8 is in its horizontal position, the first rod 17 projects from the lower end portion of the plunger 16 in the interior of the plunger hole 19 and therefore the first arm 6*a* is in a pivotal state with respect to the ultrasonic diagnostic apparatus body 2.

A description will now be given about the position of the first rod hole 18. The first rod hole 18 is formed on a circular path of the first rod 17 described with a pivotal motion of the first arm 6*a*. The first rod hole 18 is formed in a position that coincides with the position of the first rod 17 when the first arm 6a assumes a position perpendicular to the front face of the ultrasonic diagnostic apparatus 1.

Figure 5:
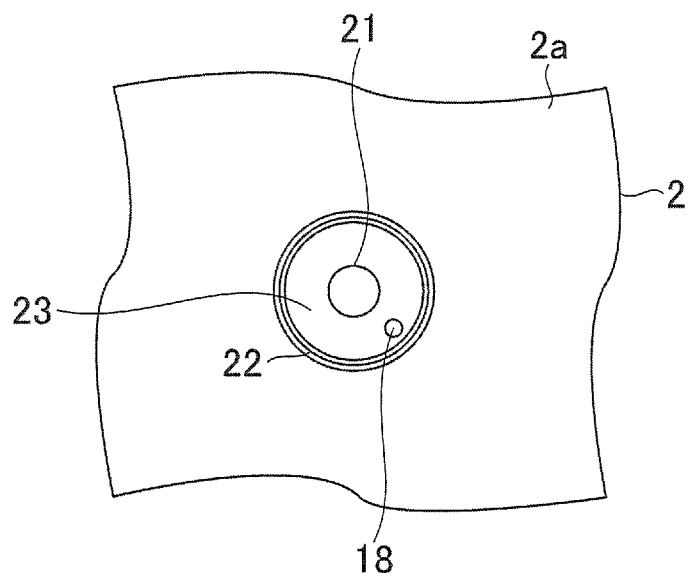
FIG. 5 is a plan view showing a portion where one end portion of the first arm is placed on an upper surface of an ultrasonic diagnostic apparatus body.

In the upper surface 2a of the ultrasonic diagnostic apparatus body 2 and in the vicinity of the first rod hole 18 is formed a support hole 21 into which the one end portion 6a1 of the first arm 6a is inserted and supported pivotally, as shown in FIG. 5. Further, in the upper surface 2a of the ultrasonic diagnostic apparatus body 2 is formed a slit 22 in a ring shape for introducing the wire 13 into the ultrasonic diagnostic apparatus body 2 from the first arm 6a. The slit 22 coincides with a movement path of the wire 13 upon pivoting of the arm 6a with respect to the ultrasonic diagnostic apparatus body 2. Numeral 23 denotes a one end placing surface on which the one end portion 6a1 of the first arm 6a is placed.

Figure 6:
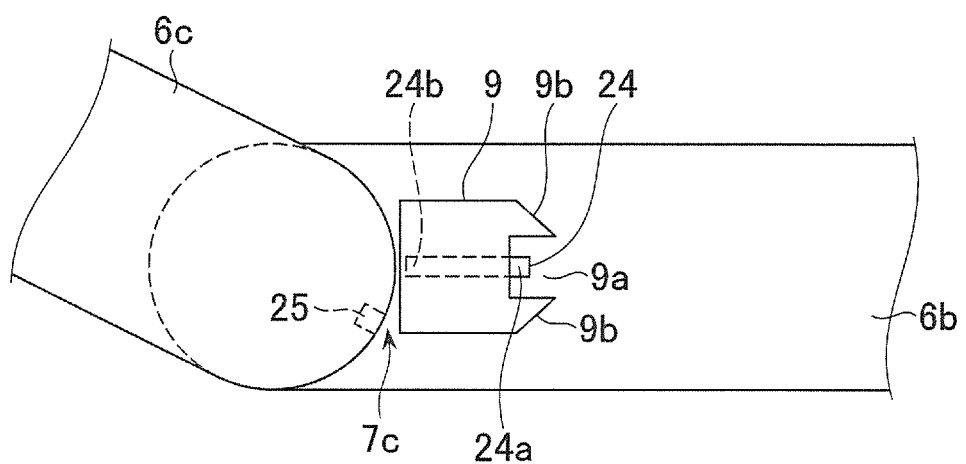
FIG. 6 is a partial enlarged bottom view of a second arm and a third arm.

Next, the third locking mechanism 7c will be described with reference to FIG. 6. The third locking mechanism 7c includes the to-be-fitted member 9, a second rod 24 provided in the to-be-fitted member 9, and a second rod hole 25 formed in the third arm 6c. More specifically, the second rod 24 is provided in the interior of the to-be-fitted member 9 and projects partially into the cutout portion 9a. One end 24a of the second rod 24 projects into the cutout portion 9a with the biasing force of a spring (not shown) disposed in the interior of the to-be-fitted portion 9. The second rod 24 has a length such that when one end 24a projects into the cutout portion 9a, an opposite end 24b does not project to the third arm 6c side.

When the hook portion 8b of the pivoting member 8, when fitted in the cutout portion 9a, pushes the second rod 24 toward the third arm 6c under the action of the spring member 11. When the position of the second rod hole 25 and that of the second rod 24 coincide with each other in the urged state of the second rod 24 toward the third arm 6c by the hook portion 8b, the opposite end 24b of the second rod 24 projects into the second rod hole 25 against the biasing force of the aforesaid spring, whereby a mutual pivoting motion of the second and third arms 6b, 6c is inhibited. The position of the second rod hole 25 and that of the second rod 24 become coincident with each other when the third arm 6c and the second arm 6b are aligned with each other.

A pair of guide faces 9b are formed on both sides of the cutout portion 9a of the to-be-fitted member 9. The guide faces 9b are formed so as to tilt on the side opposite to the cutout portion 9a. The guide faces 9b are formed respectively at positions where the hook portion 8b can come into abutment against a guide face 9b by pivoting at least one of the first and second arms 6a, 6b. The hook portion 8b comes into fitting engagement in the cutout portion 9a while sliding on the guide face 9b.

When the position of the second rod 24 and that of the second rod hole 25 do not overlap each other, even if the hook portion 8b is fitted in the cutout portion 9a and pushes the second rod 24, one end 24a of the second rod 24 remains projected to the cutout portion 9a and the opposite end 24b is in abutment against the third arm 6c. At this time, the hook portion 8b fitted in the cutout portion 9a assumed a half-fitted state because one end 24a of the second rod 24 projects to the cutout portion 9a. When the second and third arms 6b, 6c are aligned with each other and the opposite end 24b of the second rod 24 projects to the second rod hole 25, the one end 24a retreats from the interior of the cutout portion 9a and the hook portion 8b is completely fitted in the cutout portion 9a.

As shown in FIG. 1, the tipping-preventing support member 5 includes a housing 26 provided sideways of the ultrasonic diagnostic apparatus body 2 and a support rod 27 disposed vertically movably within the housing 26.

Upper and lower end portions of the support rod 27 are in a projected state from the housing 26. The lower end portion of the support rod 27 serves as a support portion that supports the ultrasonic diagnostic apparatus body 2 on the installation surface F.

The support portion 28 supports the ultrasonic diagnostic apparatus body 2 when it is at its descended position corresponding to the lowest position and is in contact with the installation surface F. A support position A supported by the support portion 28 always lies on the protruding direction D side of the display unit 3 with respect to a centroid projected position GF resulting from projecting the center of gravity of the ultrasonic diagnostic apparatus 1 downwards onto the installation surface F in the vertical direction (see FIGS. 1 and 7).

A description will now be given about the support position A. As shown in FIG. 7, even when the display unit 3 protrudes from the ultrasonic diagnostic apparatus body 2 and the centroid projected position GF has shifted to the protruding direction D side to a greater extent than a support position B where the ultrasonic diagnostic apparatus body 2 is supported by the wheels 4, the support position A lies on the protruding direction D side with respect to the shifted centroid projected position GH. Even when the arm 6 is extended to a maximum extent, resulting in the display unit 3 assuming a position remotest from the ultrasonic diagnostic apparatus body 2, the support position A lies on the protruding direction D side with respect to the shifted centroid projected position GH.

In the interior of the housing 26 disposed locking means (not shown) which, when the support portion 28 is in its descended position, as shown in FIG. 1, inhibits the vertical movement of the support rod 27 and holds the descended position. Likewise, in the interior of the housing 26 is disposed locking means (not shown) which, when the support portion 28 is in its ascended position corresponding to the highest position, as shown in FIG. 8, inhibits the vertical movement of the support rod 27 and holds the ascended position.

A connecting rod 29 is connected to the support rod 27. The wire 13 is connected to an end portion of the connecting rod 29 on the side opposite to the support rod 27. Therefore, as the support rod 27 descends, the wire 13 is pulled downwards and the pivoting member 8 moves toward its horizontal position (see FIG. 4B). On the other hand, when the inhibition of the locking means which holds the descended position is cancelled, the pivoting member 8 pivots in the vertical direction (see FIG. 4A) under the action of the spring 11 (see FIGS. 4A and 4B), so that the wire 13 pulls up the connecting rod 29 and the rod 27 rises.

The wheels 4 are provided four in all at the four corners of the lower portion of the ultrasonic diagnostic apparatus body 2. At least when the arm 6 is at its home position, the ultrasonic diagnostic apparatus body 2 can be supported by only the wheels 4. The wheels 4 are an example of the support member defined in the invention.

Figure 8:
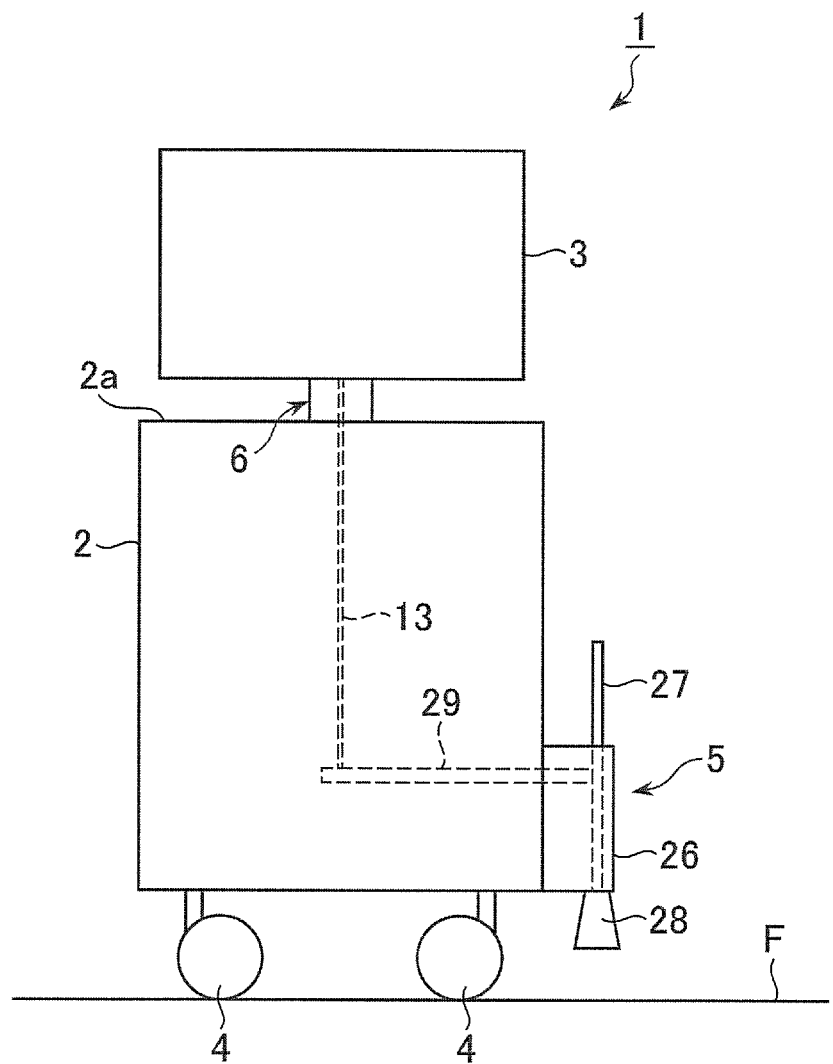
FIG. 8 is a front view with a support portion lying at its raised position in the ultrasonic diagnostic apparatus of the first embodiment.

In the ultrasonic diagnostic apparatus 1 of this embodiment, when the arm 6 is at its home position and the support portion 28 is at its ascended position as shown in FIG. 8, the arms 6a-6c are inhibited from pivoting by the locking mechanisms 7a-7c. Therefore, in the case where the support portion 28 is at its ascended position for example when moving the ultrasonic diagnostic apparatus 1, the arm 6 is at its home position and it is impossible to move the display unit 3. Thus, it is possible to prevent tipping of the ultrasonic diagnostic apparatus 1 which is caused by protrusion of the display unit 3 from the ultrasonic diagnostic apparatus body 2.

On the other hand, when the support portion 28 is moved to its descended position as shown in FIG. 1, the pivoting member 8 moves to its horizontal position and the inhibition of pivoting of the arms 6a-6c by the locking mechanisms 7a-7c is cancelled. As a result, as shown for example in FIG. 7, it is possible to pivot the arms 6a-6c and thereby move the display unit 3 to a position where the operator can see the display unit more easily. At this time, tipping of the ultrasonic diagnostic apparatus 1 can be prevented because the ultrasonic diagnostic apparatus body 2 can be supported by the support portion 28.

Figure 9:
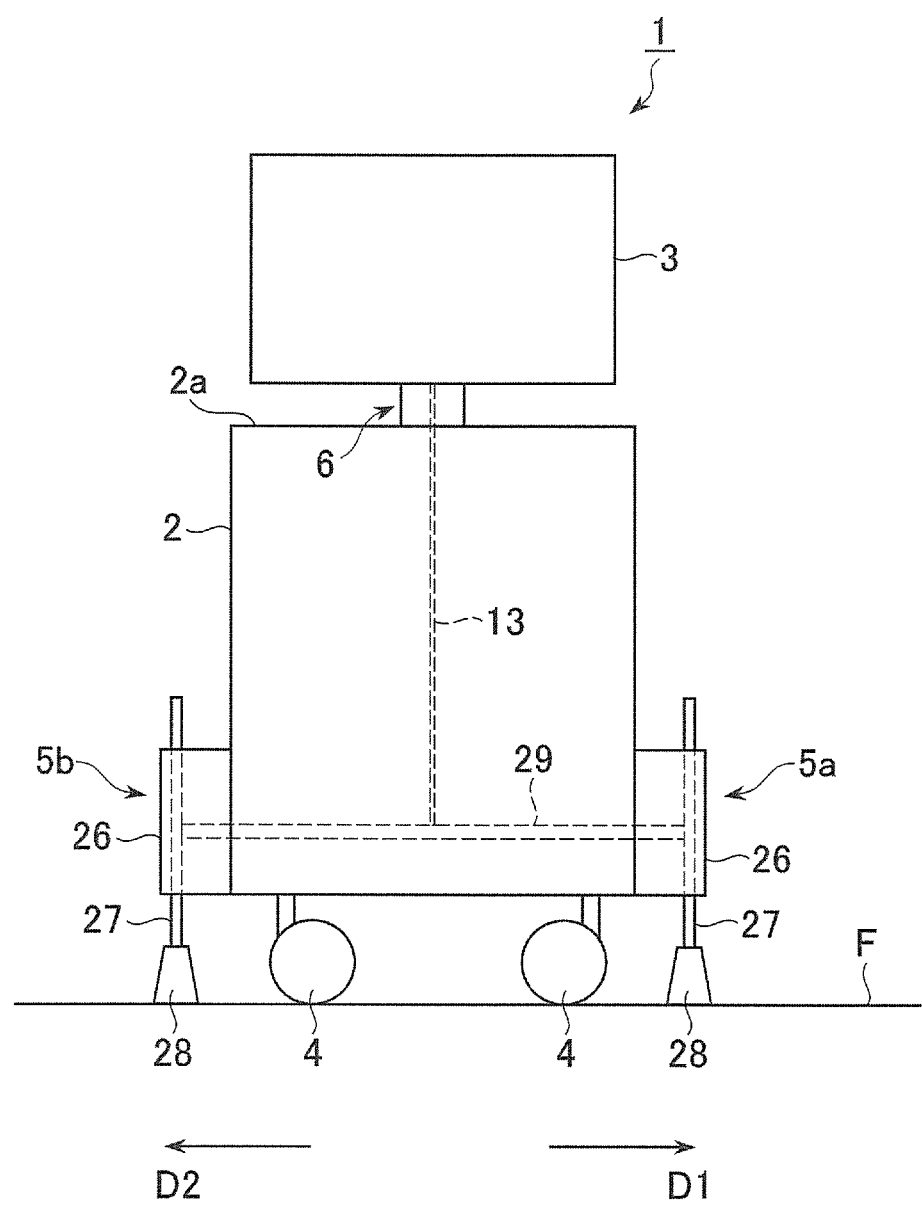
FIG. 9 is a front view showing an ultrasonic diagnostic apparatus according to a first modification of the first embodiment.

Next, a description will be given about modifications of the first embodiment. A first modification will first be described with reference to FIG. 9. In an ultrasonic diagnostic apparatus 1 according to the first modification, a total of two tipping-preventing support members 5a and 5b are provided on both side faces respectively of the ultrasonic diagnostic apparatus body 2. With the tipping-preventing support members 5a and 5b, the ultrasonic diagnostic apparatus body 2 can be supported by the support portion 28 even when the display unit 3 protrudes to both sides, that is, a protruding direction D1 side and a protruding direction D2, of the ultrasonic diagnostic apparatus body 2.

In this modification, the connecting rod 29 is connected to a support rod 27 of the tipping-preventing support member 5a and also to a support rod 27 of the tipping-preventing support member 5b, so that vertical movements of both support rods 27 are interlocked with each other. The wire 13 is connected to an approximately intermediate portion of the connecting rod 29.

Figure 10:
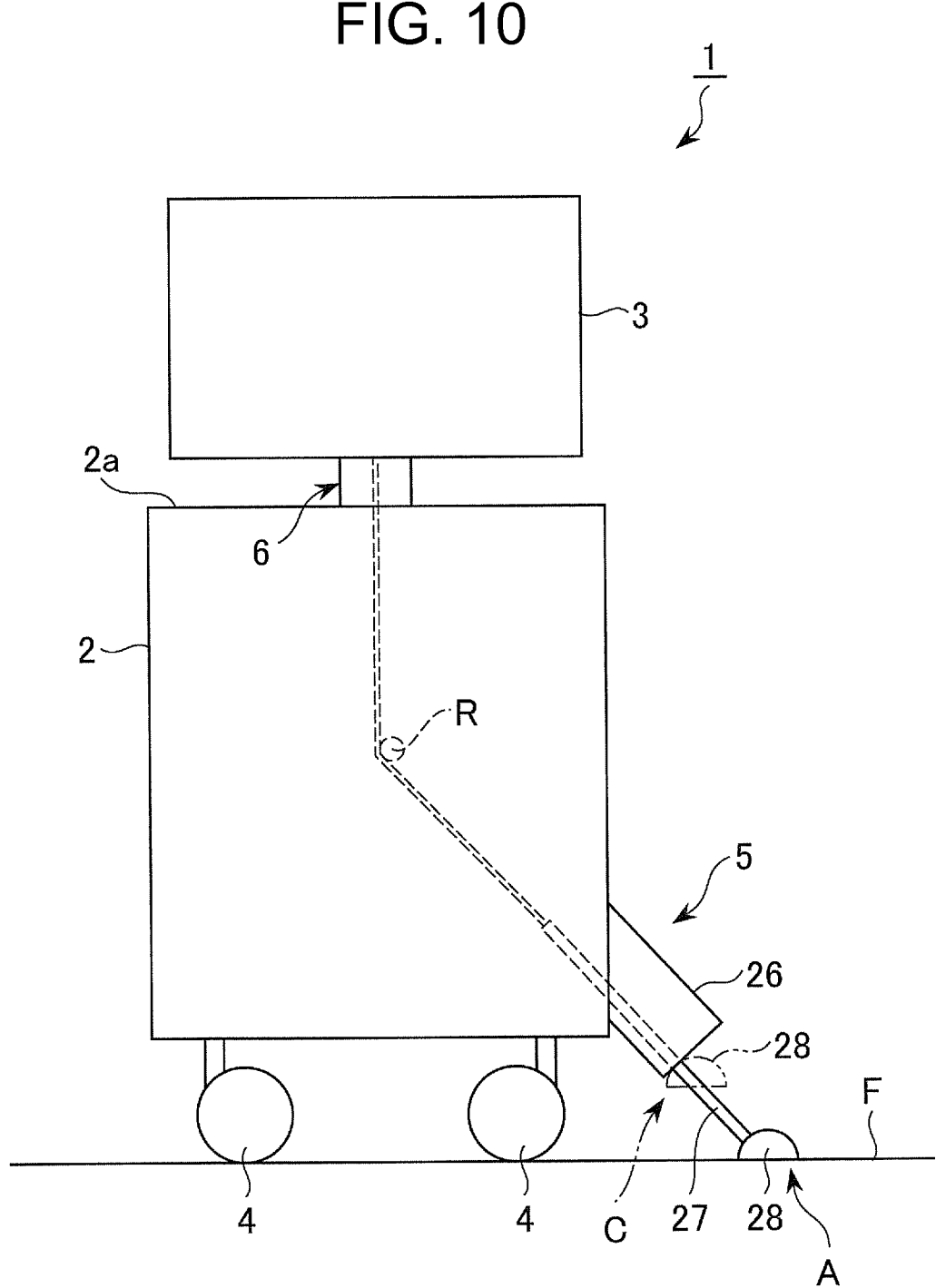
FIG. 10 is a front view showing an ultrasonic diagnostic apparatus according to a second modification of the first embodiment.

Next, a second modification will be described with reference to FIG. 10. In this second modification, the housing 26 of the tipping-preventing support member 5 is mounted aslope relative to a side face of the ultrasonic diagnostic apparatus body 2 and is inclined relative to the installation surface F. As a result, the support rod 27 is inclined relative to the installation surface F and is adapted to move up and down in the inclined direction. By such an up-and-down movement in the inclined direction of the support rod 27 the support portion 28 can move between a support position A and a stand-by position C. The support position A indicates a position at which the support portion 28 assumes its descended position corresponding the lowest position and is in contact with the installation surface F, while the stand-by position C indicates a position at which the support portion 28 assumes its ascended position corresponding to the highest position.

Also in the interior of the housing 26 according to this second modification there are disposed locking means for holding the descended position of the support portion 28 and locking means for holding the ascended position of the support portion 28 (neither of the locking means is shown).

In this second modification, a roller R is fixed in the interior of the ultrasonic diagnostic apparatus body 2. The wire 13 is guided by the roller R within the ultrasonic diagnostic apparatus body 2 and it is connected to the upper end of the support rod 27. When the support portion 28 is at its ascended position, i.e., the stand-by position C, the pivoting motion of the arms 6a-6c is inhibited by the locking mechanisms 7a-7c. On the other hand, when the support portion 28 is at its descended position, i.e., the support position A, the inhibition of pivoting of the arms 6a-6c by the locking mechanisms 7a-7c is cancelled.

According to this second modification, since the support rod 27 is adapted to move up and down in the inclined direction, the support position A by the support portion 28 can be set at a position spaced as distant as possible from the ultrasonic diagnostic apparatus body 2, and even if the display unit 3 is moved to a position more distant from the ultrasonic diagnostic apparatus body 2, it is possible to prevent tipping of the ultrasonic diagnostic apparatus 1. Moreover, when the support portion 28 is in the stand-by position C, it is closer to the ultrasonic diagnostic apparatus body 2 than in the support position A. Therefore, when moving the ultrasonic diagnostic apparatus 1, the support rod 27 can be prevented from becoming an obstacle by locating the support portion 28 in the stand-by position C.

Second Embodiment

Figure 12:
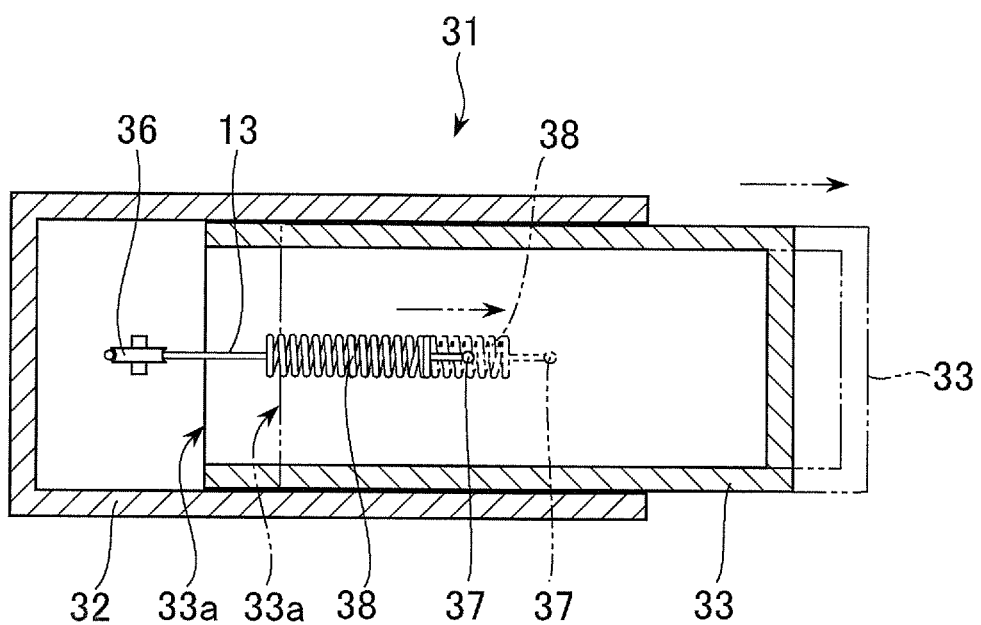
FIG. 12 is a sectional view taken on line X-X in FIG. 11.
Figure 13:
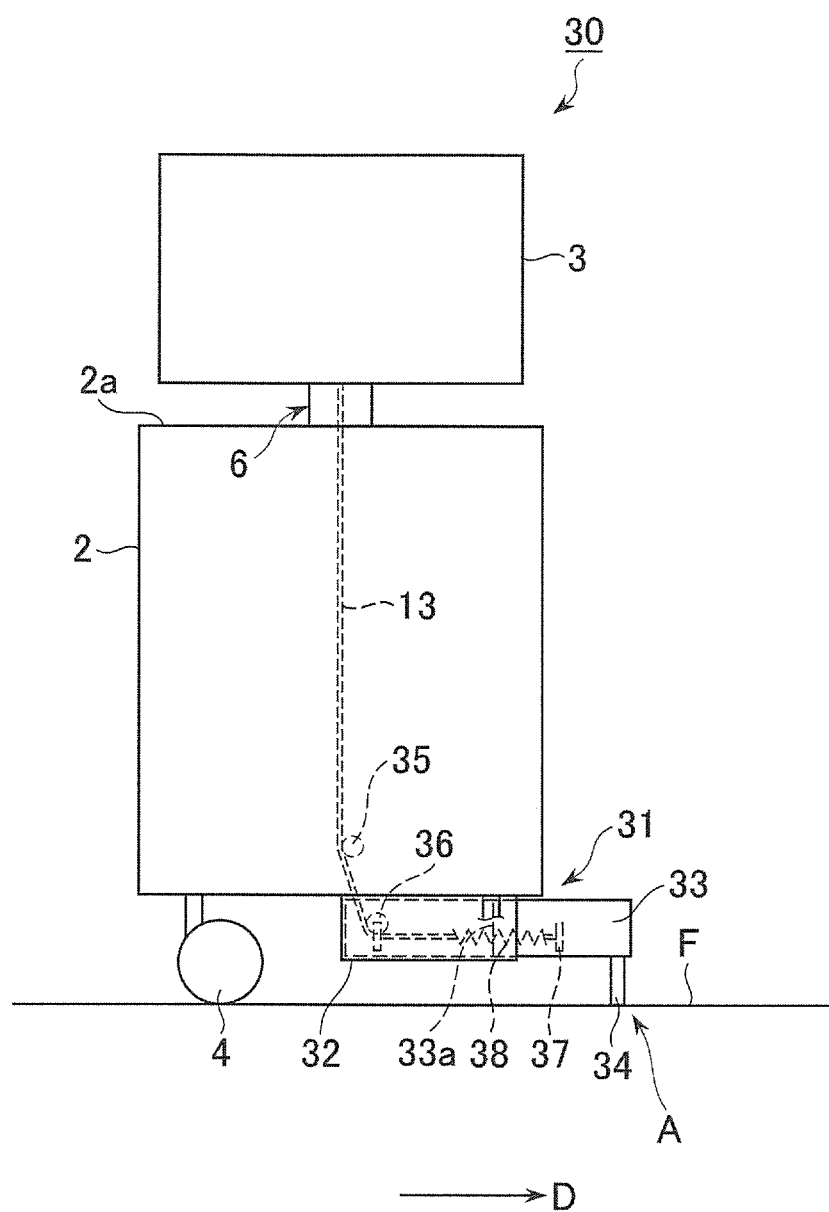
FIG. 13 is a front view showing a slid state of a slide arm from its state shown in FIG. 14 in the ultrasonic diagnostic apparatus of the second embodiment.

A second embodiment of the invention will be described below with reference to FIGS. 11 to 13. As to the same constructional portions as in the first embodiment, they are identified by the same reference numerals as in the first embodiment and explanations thereof will be omitted.

In an ultrasonic diagnostic apparatus 30 of this second embodiment, a tipping-preventing support member 31 is provided in a lower portion of the ultrasonic diagnostic apparatus body 2. The tipping-preventing support member 31 includes a storage housing 32 provided in the lower portion of the ultrasonic diagnostic apparatus body 2 and a slide arm 33 disposed slidably in and projecting from the interior of the storage housing 32.

The interior of the slide arm 33 is hollow and an end portion thereof located on the storage housing 32 side opens to form an opening 33a. A rod-like support portion 34 is provided on the underside of the projecting portion of the slide arm 33 projecting from the storage housing 32. The support portion 34 supports the ultrasonic diagnostic apparatus body 2. The support portion 34 has a length up to a vicinity of the installation surface F, not reaching the installation surface F. Consequently, the slide arm 33 can be allowed to slide smoothly without the support portion 34 coming into contact with the installation surface F. Upon tilting of the ultrasonic diagnostic apparatus body 2 the support portion 34 comes into contact with the installation surface F to support the ultrasonic diagnostic apparatus body 2.

As the slide arm 33 slides within the storage housing 32, the support portion 34, while describing a rectilinear path in the horizontal direction, can move between a support position A (see FIG. 13) able to support the ultrasonic diagnostic apparatus body 2 and a stand-by position C (see FIG. 11) at which the support portion 34 is located just under the ultrasonic diagnostic apparatus body 2. When the support portion 34 reaches the support position A, the pivoting member 8 reaches its horizontal position and the inhibition of movement of the arms 6a-6c by the locking mechanisms 7a-7c is cancelled. The details of this point will be described later.

As in the first embodiment, the support position A lies always on the protruding direction D side with respect to the centroid projected position GF (not shown in this embodiment).

In this embodiment the wire 13 is guided through the interior of the ultrasonic diagnostic apparatus body 2 and the interior of the storage housing 32 by both a body-side guide roller 35 fixed to the ultrasonic diagnostic apparatus body 2 and a storage housing-side guide roller 36 disposed within the storage housing 32. The wire 13 is introduced from the opening 33a into the slide arm 33 and is fixed to a stationary rod 37 provided on an inner bottom 33b of the slide arm 33.

An adjusting spring 38 is disposed on the wire 13 and between the storage housing-side guide roller 36 and the stationary rod 37. A spring constant of the adjusting spring 38 is set in relation to the spring constant of the spring member 11 (see FIG. 4) which urges the pivoting member 8 toward one end portion 6a1 side of the first arm 6a so that the pivoting member 8 reaches its horizontal position when the support portion 34 reaches the support position A. More specifically, the spring constant of the adjusting spring 38 is set so that the wire 13 moves and the pivoting member 8 pivots up to its horizontal position against the pulling force of the spring member 11 when the slide arm 33 is slid in the protruding direction D of the display unit 3 and the support portion 34 reaches the support position A. Therefore, even if the slide arm 33 is slid in the protruding direction D, if the support portion 34 has not reached the support position A yet, the pivoting member 8 maintains its vertical position with the pulling force of the spring member 11 and, as indicated by a dot-dash line in FIG. 12, the wire 13 does not change its position, but only the adjusting spring 38 extends.

Upon arrival of the support portion 34 at the support position A the adjusting spring 38 extends to its maximum length for an instant and then contracts, whereby the wire 13 is pulled and the pivoting member 8 moves from the vertical position to the horizontal position.

Figure 11:
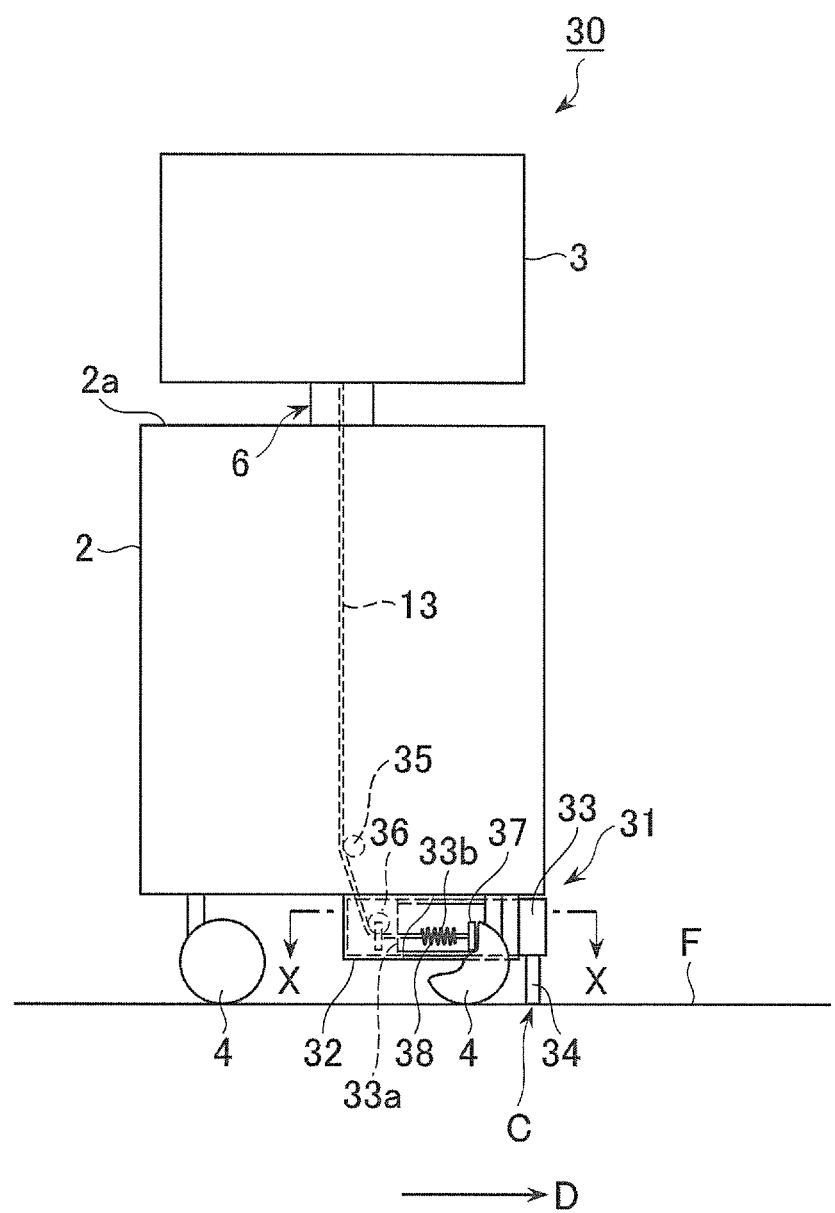
FIG. 11 is a partially cutaway front view showing an ultrasonic diagnostic apparatus according to a second embodiment of the invention.

In the ultrasonic diagnostic apparatus 30, as shown in FIG. 11, when the support portion 34 is at the stand-by position C and the arm 6 is at the home position, the pivoting of the arms 6a-6c (none of them are shown in this embodiment) is inhibited by the locking mechanisms 7a-7c, as in the first embodiment. Therefore, also in this second embodiment the display unit 3 cannot be moved when the support portion 34 is held at the stand-by position C, for example when moving the ultrasonic diagnostic apparatus 30, and hence it is possible to prevent tipping of the ultrasonic diagnostic apparatus 1.

On the other hand, when the slide arm 33 is slid to move the support portion 34 up to the support position A, the wire 13 is pulled and moved by the slide arm 33 and the pivoting member 8 moves up to its horizontal position. Consequently, as in the first embodiment, the inhibition of pivotal motion of the arms 6a-6c by the locking mechanism 7a-7c is cancelled and the display unit 3 becomes movable. Also in this second embodiment it becomes possible at this time to support the ultrasonic diagnostic apparatus body 2 by the support portion 34 and hence possible to prevent tipping of the ultrasonic diagnostic apparatus 30.

Third Embodiment

Figure 14:
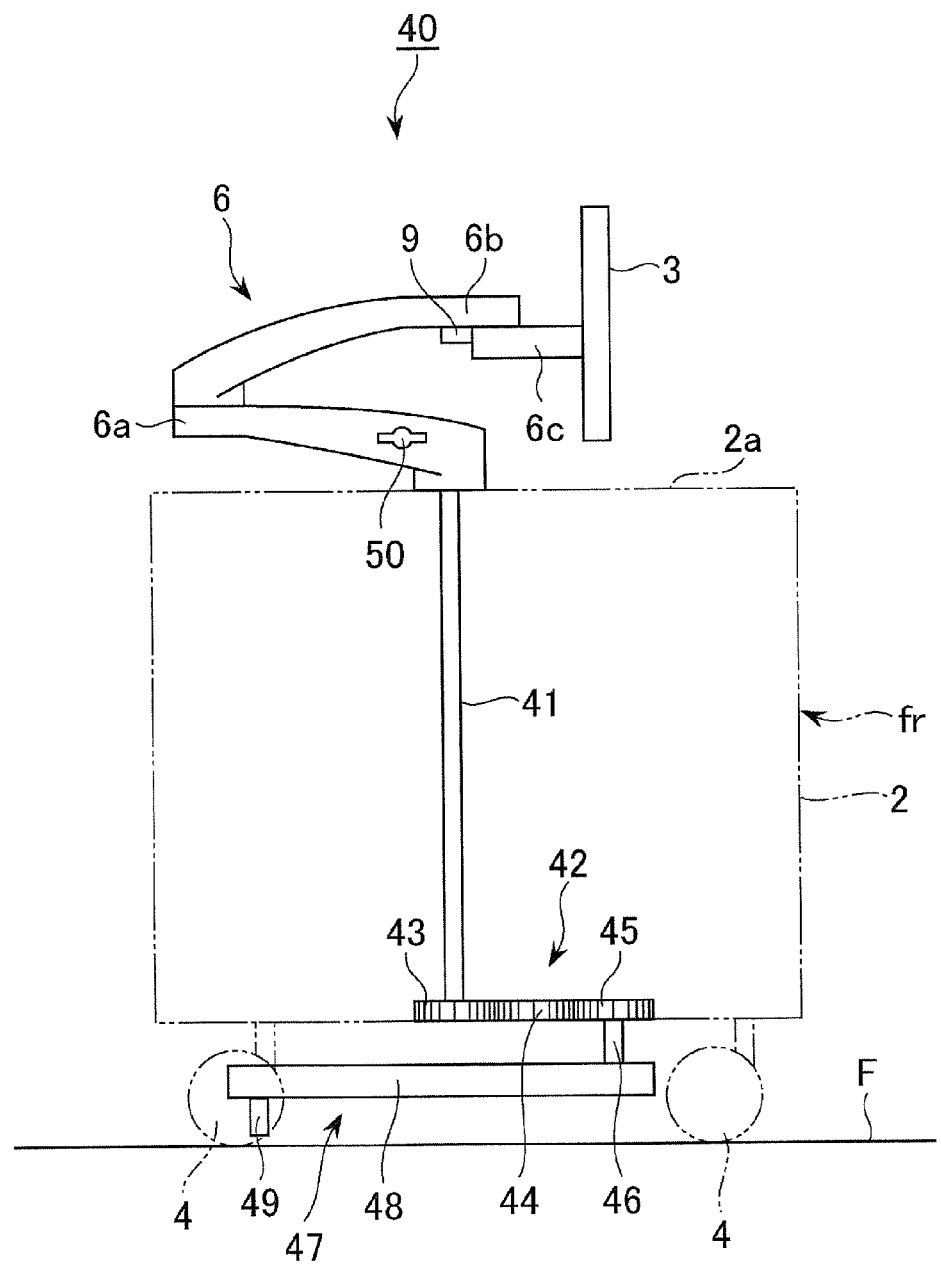
FIG. 14 is a side view showing a schematic configuration of an ultrasonic diagnostic apparatus according to a third embodiment of the invention.
Figure 15:
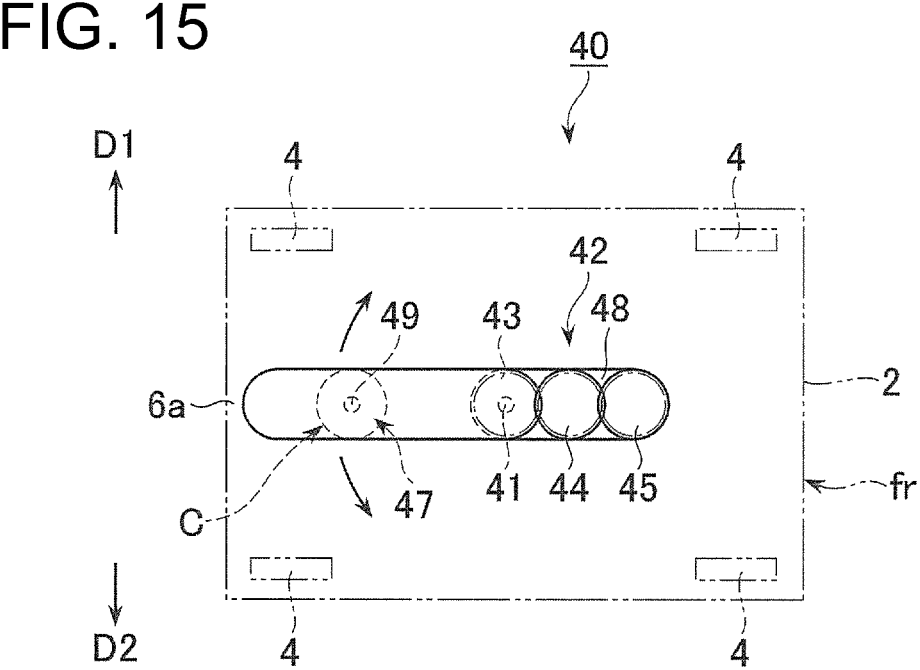
FIG. 15 is a plan view showing a schematic configuration of the ultrasonic diagnostic apparatus of FIG. 14.
Figure 16:
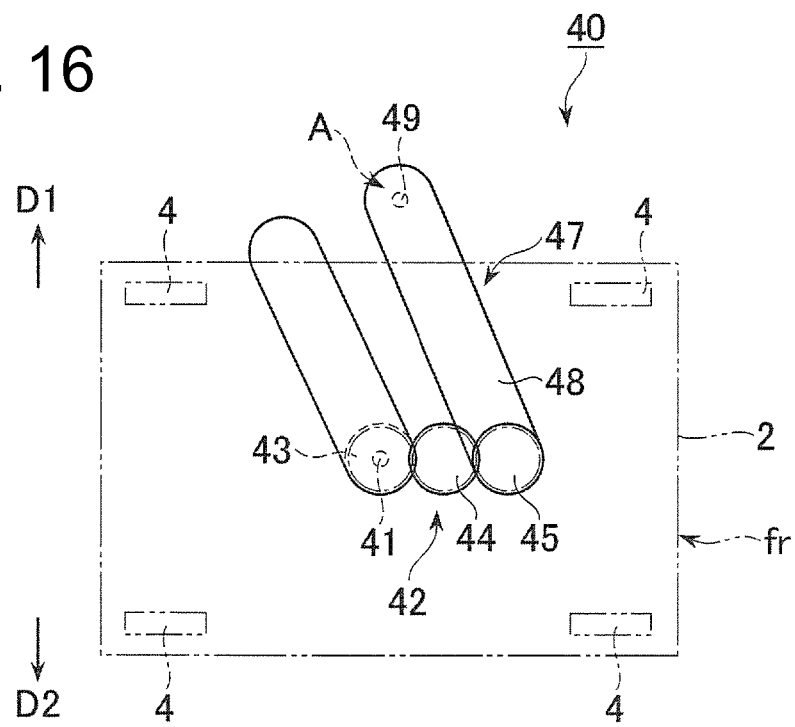
FIG. 16 is a plan view showing a pivoted state of a first arm and a support arm from the state shown in FIG. 15.

A third embodiment of the invention will now be described with reference of FIGS. 14 to 16. In FIGS. 14 to 16, the same constructional portions as in the first or the second embodiment are identified by the same reference numerals as in the first or the second embodiment and explanations thereof will be omitted.

In FIGS. 14 to 16, the ultrasonic diagnostic apparatus body 2 and the wheels 4 are indicated by dash-double dot lines. In both plan views of FIGS. 15 and 16, the second arm 6b, third arm 6c and display unit 3 are not shown. The locking mechanism 7 and the storage hole 10 formed in the first arm 6a are not shown, either.

In the ultrasonic diagnostic apparatus 40, a shaft 41 extends downwards through the interior of the ultrasonic diagnostic apparatus body 2 from the lower portion of the first arm 6a. A gear mechanism 42 is disposed in the lower portion of the ultrasonic diagnostic apparatus body 2. The gear mechanism 42 includes a first gear 43, a second gear 44 meshing with the first gear 43, an a third gear 45 meshing with the second gear 44.

The first gear 43 is provided at a lower end of the shaft 41. In the third gear 45 is provided a shaft 46 so as to project from the underside of the ultrasonic diagnostic apparatus body 2, with a tipping-preventing support member 47 being mounted on the shaft 46.

The tipping-preventing support member 47 is made up of a support arm 48 having an upper surface with the shaft 46 provided thereon and a rod-like support portion 49 projecting from a lower surface of the support arm 48. The support portion 49 supports the ultrasonic diagnostic apparatus body 2. As will be described later, the support arm 48 is adapted to pivot in the horizontal direction, whereby the support portion 49, while describing a circular path, can move between a support position A (see FIG. 16) able to support the ultrasonic diagnostic apparatus body 2 and a stand-by position C (see FIG. 15) at which the support arm 48 faces in a direction perpendicular to a front face fr of the ultrasonic diagnostic apparatus body 2.

As will be described later, the support arm 48 is adapted to pivot the shaft 46 in interlock with the first arm 6a. The support position A shown in FIG. 16 is an example and it is adapted to move with pivotal motion of the first arm 6a. Provided, however, that the position which the support portion 49 assumes when located on the protruding direction D side of the display unit 3 with respect to the wheels 4 is defined to be the support position A. In the ultrasonic diagnostic apparatus 1, even if the centroid projected position GF (not shown in this embodiment) shifts with movement of the display unit 3 caused by pivoting of the first arm 6a, the support portion 49 moves with pivoting of the first arm 6a so that the support position A always lies on the protruding direction D1 side or D2 side with respect to the centroid projected position GF.

When the support portion 49 is not positioned on the protruding direction D side of the display unit 3 with respect to the wheels 4 (when the support portion 49 is stored in the lower portion of the ultrasonic diagnostic apparatus body 2), the ultrasonic diagnostic apparatus body 2 can be supported by only the wheels 4.

The support portion 49 has a length reaching a vicinity of the installation surface F, not reaching the installation surface F. Consequently, when the support arm 48 is pivoted, the support portion 49 can be pivoted smoothly without contacting the installation surface F. Upon tilting of the ultrasonic diagnostic apparatus body 2 the support portion 49 comes into contact with the installation surface F and supports the ultrasonic diagnostic apparatus body 2.

The ultrasonic diagnostic apparatus 40 of this embodiment is not provided with the wire 13. A pivoting knob 50 provided on a side face of the first arm 6a is attached to a fulcrum of the pivoting member 8. The pivoting member 8 (see FIG. 4) can be pivoted by turning the pivoting knob 50.

In the ultrasonic diagnostic apparatus 40 of this embodiment, as shown in FIGS. 14 and 15, with the arm 6 lying at its home position, the inhibition of pivotal motion by the locking mechanisms 7a-7c is cancelled and the arms 6a-6c are pivoted to move the display unit 3 up to a position where the operator is easy to see the display unit. At this time, with a pivotal motion of the first arm 6a, the shaft 41 rotates and so does the first gear 43. The rotation of the first gear 43 is transmitted to the third gear 45 by the second gear 44 and, with this rotation of the third gear 45, the support arm 48 pivots about the shaft 46 in the same direction as the first arm 6a.

According to this third embodiment, for example when moving the ultrasonic diagnostic apparatus 40, it is possible, by locating the support arm 48 at the stand-by position C, to prevent the support arm 48 from becoming an obstacle. Moreover, if the display unit 3 is moved when using the ultrasonic diagnostic apparatus 40, the support portion 49 can be brought to the support position A with the movement of display unit 3, so that it is possible to prevent tipping of the ultrasonic diagnostic apparatus 40. Thus, in this embodiment, since the support portion 49 moves in interlock with the movement of the display unit 3, it is possible to surely prevent tipping of the ultrasonic diagnostic apparatus 40.

Although the invention has been described above by way of embodiments thereof, it goes without saying that various changes may be made within the scope not altering the gist of the invention. For example, in the first embodiment, the descended position as the lowest position of the support portion 28 may be a vicinity of the installation surface F, not reaching the installation surface F. In this case, upon tilting of the ultrasonic diagnostic apparatus body 2, the support portion 28 comes into contact with the installation surface F and supports the ultrasonic diagnostic apparatus body 2.

Further, in the second and third embodiments, the support portions 34 and 49 may each have a length contacting the installation surface F. In this case, it is desirable that the support portions 34 and 49 be configured so as to be vertically movable. It is desirable that the inhibition of pivotal motion of the arms 6a-6c by the locking mechanisms 7a-7c be cancelled when the support portions 34 and 49 are each at the descended position contacting the installation surface F.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic diagnostic apparatus comprising:
an ultrasonic diagnostic apparatus body;
a support member provided in the ultrasonic diagnostic apparatus body to support the ultrasonic diagnostic apparatus body on an installation surface;
a movable display provided in the ultrasonic diagnostic apparatus body;
a movable arm coupled to the movable display, the movable arm protruding from the ultrasonic diagnostic apparatus body in a direction away from the ultrasonic diagnostic apparatus body, the movable arm configured to pivot in a horizontal direction;
a tipping-preventing support member provided in the ultrasonic diagnostic apparatus body and comprising a support portion configured to support the ultrasonic diagnostic apparatus body on the installation surface on the protruding side of the movable display with respect to the support member, wherein the support portion of the tipping-preventing support member is movable between a support position able to support the ultrasonic diagnostic apparatus body and a stand-by position closer to the ultrasonic diagnostic apparatus body than the support position, wherein the support portion is configured to ascend and descend with respect to the installation surface and, when in a descended position, the support portion is configured to support the ultrasonic diagnostic apparatus body on the installation surface, wherein the support portion provides support between the support position and the stand-by position by moving in an inclined direction relative to the installation surface; and
a movement inhibition device coupled to the tipping-preventing support member, the movement inhibition device configured to inhibit the movable display from pivoting in the horizontal direction when the support portion is in the stand-by position and configured to cancel the inhibition of the pivoting of the movable display when the support portion is in the support position.

2. An ultrasonic diagnostic apparatus according to claim 1, wherein a support position on the installation surface by the support portion of the tipping-preventing support member is on the protruding side of the movable body with respect to a centroid projected position resulting from projecting a center of gravity of the ultrasonic diagnostic apparatus onto the installation surface downwards in a vertical direction.

3. An ultrasonic diagnostic apparatus according to claim 1, wherein the descended position of the support portion is one of a position where the support portion is in contact with the installation surface and a position where the support portion has reached a vicinity of the installation surface.

4. An ultrasonic diagnostic apparatus according to claim 1, wherein when the movable display is interlocked with the support portion of the tipping preventing support.

5. An ultrasonic diagnostic apparatus according to claim 1, wherein the support portion of the tipping-preventing support member is movable between the support position and the stand-by position along a circular path in a horizontal direction.

6. An ultrasonic diagnostic apparatus according to claim 1, wherein the support portion of the tipping-preventing support member is movable between the support position and the stand-by position along a rectilinear path in a horizontal direction.

7. An ultrasonic diagnostic apparatus according to claim 1, wherein the movable display comprises a flat panel display.

8. An ultrasonic diagnostic apparatus according to claim 2, wherein the movable display comprises a flat panel display.

9. An ultrasonic diagnostic apparatus according to claim 1, wherein the movable display comprises a flat panel display.

10. An ultrasonic diagnostic apparatus according to claim 1, wherein the support member comprises a wheel provided in a lower portion of the ultrasonic diagnostic apparatus body.

11. An ultrasonic diagnostic apparatus according to claim 2, wherein the support member comprises a wheel provided in a lower portion of the ultrasonic diagnostic apparatus body.

* * * * *